United States Patent
Olubummo et al.

(10) Patent No.: US 11,760,894 B2
(45) Date of Patent: Sep. 19, 2023

(54) FUSING AGENT INCLUDING A METAL BIS(DITHIOLENE) SALT

(71) Applicant: Hewlett-Packard Development Company, L.P., Spring, TX (US)

(72) Inventors: Paul Olubummo, Palo Alto, CA (US); Lihua Zhao, Palo Alto, CA (US); Aja Hartman, Palo Alto, CA (US); Howard S. Tom, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 17/859,850

(22) Filed: Jul. 7, 2022

(65) Prior Publication Data
US 2022/0372316 A1 Nov. 24, 2022

Related U.S. Application Data

(63) Continuation of application No. 16/488,662, filed as application No. PCT/US2017/058122 on Oct. 24, 2017, now Pat. No. 11,414,561.

(51) Int. Cl.
| | | |
|---|---|---|
| C09D 11/38 | (2014.01) | |
| B33Y 70/00 | (2020.01) | |
| B29C 64/314 | (2017.01) | |
| B33Y 40/10 | (2020.01) | |
| C07F 15/04 | (2006.01) | |
| C09D 11/033 | (2014.01) | |

(52) U.S. Cl.
CPC ............ *C09D 11/38* (2013.01); *B29C 64/314* (2017.08); *B33Y 40/10* (2020.01); *B33Y 70/00* (2014.12); *C07F 15/045* (2013.01); *C09D 11/033* (2013.01)

(58) Field of Classification Search
CPC ..... B29C 64/165; B29C 64/314; B33Y 40/10; B33Y 70/00; C07C 319/12; C07F 15/045; C09D 11/033; C09D 11/38
See application file for complete search history.

(56) References Cited

U.S. PATENT DOCUMENTS

| | | | |
|---|---|---|---|
| 5,089,585 A * | 2/1992 | Reynolds ........... | C08G 18/3897 252/587 |
| 7,204,941 B2 | 4/2007 | Hall et al. | |
| 7,441,887 B2 | 10/2008 | Senga et al. | |
| 8,449,101 B2 | 5/2013 | Yokoi | |
| 9,550,902 B1 | 1/2017 | Sakamoto et al. | |
| 9,587,309 B1 | 3/2017 | Pickens et al. | |
| 2009/0085256 A1 | 4/2009 | Mataki | |
| 2017/0247561 A1 | 8/2017 | Nakagawa et al. | |
| 2018/0354191 A1* | 12/2018 | Nauka ................... | B33Y 30/00 |

FOREIGN PATENT DOCUMENTS

WO   2017/014785 A1   1/2017

* cited by examiner

*Primary Examiner* — Sanza L. McClendon
(74) *Attorney, Agent, or Firm* — HP Inc. Patent Department (57) ABSTRACT

An example of a fusing agent includes a metal bis(dithiolene) salt, a polar aprotic solvent, and a balance of water. An example of a method for making an example of the fusing agent includes adding a metal bis(dithiolene) salt into a liquid vehicle including at least a polar aprotic solvent and water.

11 Claims, 4 Drawing Sheets

100

ADDING A METAL BIS(DITHIOLENE) SALT INTO A LIQUID VEHICLE INCLUDING AT LEAST A POLAR APROTIC SOLVENT AND WATER — 102

FUSING AGENT INCLUDING A METAL BIS(DITHIOLENE) SALT

CROSS-REFERENCE TO RELATED APPLICATIONS

This application is a continuation of U.S. application Ser. No. 16/488,662, filed Aug. 26, 2019, which itself is a national stage entry under 35 U.S.C. § 371 of PCT/US2017/058122, filed Oct. 24, 2017, each of which is incorporated by reference herein in its entirety.

BACKGROUND

Three-dimensional (3D) printing may be an additive printing process used to make three-dimensional solid parts from a digital model. 3D printing is often used in rapid product prototyping, mold generation, mold master generation, and short run manufacturing. Some 3D printing techniques are considered additive processes because they involve the application of successive layers of material. This is unlike traditional machining processes, which often rely upon the removal of material to create the final part. Some 3D printing methods use chemical binders or adhesives to bind build materials together. Other 3D printing methods involve at least partial curing or fusing or melting of the build material. For some materials, at least partial melting may be accomplished using heat-assisted extrusion, and for some other materials (e.g., polymerizable materials), curing or fusing may be accomplished using, for example, ultraviolet light or infrared light.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

In examples of the three-dimensional (3D) printing method and the 3D printing system disclosed, an entire layer of a build material (also referred to as build material particles) is exposed to radiation, but a selected region (in some instances less than the entire layer) of the build material is fused and hardened to become a layer of a 3D part. A fusing agent is selectively deposited in contact with the selected region of the build material. The fusing agent(s) is capable of penetrating into at least void spaces between the build material particles, and spreading onto the exterior surface of the build material particles. This fusing agent is capable of absorbing radiation and converting the absorbed radiation to thermal energy, which in turn melts or sinters the build material that is in contact with the fusing agent. This causes the build material to fuse, bind, cure, etc. to form the layer of the 3D part.

As used herein, the terms "3D printed part," "3D part," or "part" may be a completed 3D printed part or a layer of a 3D printed part.

Some fusing agents tend to have significant absorption (e.g., 80%) in the visible region (400 nm-780 nm). This absorption generates heat suitable for fusing during 3D printing, which leads to 3D parts having mechanical integrity and relatively uniform mechanical properties (e.g., strength, elongation at break, etc.). This absorption, however, results in strongly colored, e.g., black, 3D parts. In some instances, it may not be desirable to generate strongly colored parts. Rather, it may be desirable to generate a part that is white, off-white, or some color other than black.

Some fusing agents include a metal bis(dithiolene) complex. The metal bis(dithiolene) complex has absorption at wavelengths ranging from 600 nm to 1600 nm. The metal bis(dithiolene) complex is capable of absorbing at least 80% of radiation having wavelengths ranging from 600 nm to 1600 nm. Moreover, the absorption maximum of the metal bis(dithiolene) complex may undergo a bathochromic shift (e.g., further into the near-infrared region toward the medium infrared region) or a hypsochromic shift (e.g., in the near-infrared region toward the visible region) depending upon the chemistry of the complex and/or the medium in which it is incorporated. Like the visible region absorbing fusing agents, the absorption of the fusing agents including the metal bis(dithiolene) complex generates heat suitable for fusing polymeric or polymeric composite build material in contact therewith during 3D printing.

Examples of the fusing agent disclosed herein are formulated with a metal bis(dithiolene) salt. It has unexpectedly been found that the metal bis(dithiolene) salt functions in a similar manner as the metal bis(dithiolene) complex. Like the metal bis(dithiolene) complex, the metal bis(dithiolene) salt also has absorption at wavelengths ranging from 600 nm to 1600 nm, and is capable of absorbing at least 80% of radiation having wavelengths ranging from 600 nm to 1600 nm. Moreover, the absorption maximum of the metal bis (dithiolene) salt may undergo the previously described bathochromic shift or hypsochromic shift depending upon the chemistry of the salt and/or fusing agent. As examples, the shift may depend upon a polar aprotic solvent present in the fusing agent and/or upon the nature of the functional group(s) attached to the salt. Like the visible region absorbing fusing agents and the metal bis(dithiolene) complex fusing agents, the absorption of the fusing agents including the metal bis(dithiolene) salt generates heat suitable for fusing polymeric or polymeric composite build material in contact therewith during 3D printing, which leads to 3D parts having mechanical integrity and relatively uniform mechanical properties (e.g., strength, elongation at break, etc.).

The fusing agent disclosed herein may be made by a one-step method which involves adding the metal bis(dithiolene) salt directly into a liquid vehicle including at least a polar aprotic solvent and water. This one-step method simplifies the process for making the fusing agent. For example, as compared to method(s) used to make the fusing agent including the metal bis(dithiolene) complex, the method disclosed herein may not involve a separate reducing process of the metal bis(dithiolene) complex.

Examples of the fusing agents disclosed herein, including the metal bis(dithiolene) salt, can be used to generate a part that is white, off-white, or some color other than black. It has been found that exposing the metal bis(dithiolene) salt to a polar aprotic solvent at room temperature (e.g., from about 18° C. to about 25° C.) may result in the salt initially changing color. It is to be understood that this change in color is not a loss of color (i.e., is not discoloration as defined herein), and the salt still readily absorbs the applied electromagnetic radiation. While not being bound to any theory, it is believed that the color change of the metal bis(dithiolene) salt may be due, at least in part, to dissolution and reduction into its ionic components. As the salt dissolves and reduces, it may change color and ultimately undergo discoloration (i.e., become at least substantially colorless). By "at least substantially colorless," it is meant that the original color of the salt changes or fades to a point that the formed part exhibits a color of the build material, a color of a colorant present in the fusing agent, or a color of a colorant subsequently applied to the build material. Thus, the fusing agent, containing the metal bis(dithiolene) salt, may be used to print white 3D parts, off-white 3D parts, or colored 3D parts.

The polar aprotic solvent may be selected to at least partially dissolve the metal bis(dithiolene) salt. The dissolution may cause a shift in the absorption maximum of the metal bis(dithiolene) salt. In some instances, the shift in the absorption maximum of the salt may enable the salt to harvest energy from the electromagnetic radiation applied during 3D printing. For example, the energy from the electromagnetic radiation may be harvested when the absorption maximum wavelength of the salt matches that of the source of radiation. As such, it may be desirable to utilize a salt and polar aprotic solvent combination that will shift the absorption maximum of the salt to the wavelength or within the wavelength range of the source of radiation. The absorbed radiation and harvested energy may fuse the portion of the polymeric or polymeric composite build material in contact with the fusing agent, and may initiate or further discoloration of the salt, even after the application of the radiation ceases.

In some examples, a thiol surfactant may be included in the fusing agent during formulation to accelerate the dissolution of the salt, facilitate the reduction of the bis(dithiolene) moiety of the salt, and stabilize the formulation. In particular, the thiol surfactant may render the salt more soluble in a vehicle of the fusing agent, thus reducing its tendency to precipitate out of the vehicle. Stabilizing the metal bis(dithiolene) moiety with the thiol surfactant may also facilitate the reduction of the metal bis(dithiolene) moiety by the polar aprotic solvent (i.e., may enable the reduction to occur at room temperature and within a few seconds) and/or improve the jettability of the fusing agent.

The fusing agent disclosed herein generally includes a liquid vehicle and the metal bis(dithiolene) salt. In an example, the liquid vehicle includes at least a polar aprotic solvent and water. As such, one example of the fusing agent includes a metal bis(dithiolene) salt, a polar aprotic solvent, and a balance of water.

The metal bis(dithiolene) salt allows the fusing agent to absorb radiation at wavelengths ranging from 600 nm to 1600 nm, which enables the fusing agent to convert enough radiation to thermal energy so that the polymeric or polymeric composite build material particles in contact with the fusing agent fuse.

Examples of the metal bis(dithiolene) salt may have a general formula I:

In general formula I, [CAT] represents a cationic moiety. Examples of [CAT] may include cations derived from hydrazine (e.g., hydrazyl), from piperidine (e.g., piperidyl, piperidinium cation), from pyridine (e.g., pyridyl, pyridinium ion), or from hexadecyltrimethylammonium bromide (e.g., hexadecyltrimethylammonium). In general formula I, M is a metal. Examples of M include nickel, zinc, platinum, palladium, and molybdenum. In general formula I, each of W, X, Y, and Z may be independently selected from hydrogen (H), a phenyl group (Ph), a phenyl group bonded to an R group (i.e., PhR), wherein R is $C_nH_{2n+1}$, or $OC_nH_{2n+1}$, or $N(CH_3)_2$, and a sulfur bonded to an R group (i.e., SR), wherein R is $C_nH_{2n+1}$, or $OC_nH_{2n+1}$, or $N(CH_3)_2$. In these examples, n may be greater than or equal to 2 and less than or equal to 12 (i.e., $2 \leq n \leq 12$). When the metal bis(dithiolene) salt has the general formula I, the strong near-infrared (NIR) absorption of the metal bis(dithiolene) salt may be the result of the electron delocalization about the dithiolene ring and the interaction of the delocalized electrons with the empty d-orbitals of the metal center.

The amount of the metal bis(dithiolene) salt in the fusing agent may range from about 1 wt % to about 3 wt % based on the total weight of the fusing agent. In an example, the amount of the metal bis(dithiolene) salt present in the fusing agent is about 1 wt % based on the total weight of the fusing agent. It is believed that these metal bis(dithiolene) salt loadings provide a balance between the fusing agent having jetting reliability and electromagnetic radiation absorbance efficiency.

In some examples, the salt disclosed herein may be purchased and incorporated into the liquid vehicle to form the fusing agent.

In other examples, the salt may be made from a metal bis(dithiolene) complex having a desirable metal (M) at the center of the complex. A general structure of such a complex is represented in (II).

wherein M is a metal selected from the group consisting of nickel, zinc, platinum, palladium, and molybdenum; each of W, X, Y, and Z is selected from the group consisting of H, Ph, PhR, and SR, wherein Ph is a phenyl group and R is selected from the group consisting of $C_nH_{2n+1}$, $OC_nH_{2n+1}$, and $N(CH_3)_2$, wherein $2 \leq n \leq 12$.

In a first example method, the salt may be made by exposing a metal bis(dithiolene) complex (e.g., general formula II) to a solution including a reducing agent, thereby forming a reduced metal bis(dithiolene) complex dissolved in the solution; diluting the solution with an aqueous vehicle so that the reduced metal bis(dithiolene) complex is present in an amount ranging from about 1% to about 3% by weight; and adding a nitrogen base to the diluted solution, thereby reacting the reduced metal bis(dithiolene) complex with the nitrogen base and forming the metal bis(dithiolene) salt. In a second example method, the salt may be made by exposing a metal bis(dithiolene) complex (e.g., general formula II) to a solution including a reducing agent, thereby forming a reduced metal bis(dithiolene) complex dissolved in the solution; and adding a nitrogen base to the solution, thereby reacting the reduced metal bis(dithiolene) complex with the nitrogen base and forming the metal bis(dithiolene) salt.

In either of the first or second example methods, the reducing agent is a polar aprotic solvent, such as 1-methyl-2-pyrrolidone (1M2P), 2-pyrrolidone, 1-(2-hydroxyethyl)-2-pyrrolidone, dimethylformamide (DMF), dimethyl sulfoxide (DMSO), or a combination thereof; and the nitrogen base may be tetraethylammonium bromide, hydrazine, piperidine, pyridine, hexadecyltrimethylammonium bromide, and combinations thereof. When combinations are used, separation of the resulting compounds may be performed. In the first example method, the aqueous vehicle used to dilute the concentration of the reduced metal bis(dithiolene) complex may include water, a water soluble organic solvent, and an additive selected from the group consisting of an emulsifier, a surface tension reduction agent, a wetting agent, a scale inhibitor, an anti-deceleration agent, a chelating agent, an antimicrobial agent, and a combination thereof. Each of these components and suitable amount of these components will be described further herein in reference to the liquid vehicle of the fusing agent.

An example of a bis(dithiolene) salt made from its corresponding bis(dithiolene) complex is tetraethylammonium nickel bis(dithiolene) salt. Using the second example method, the salt is made from a two part reaction. First, a nickel bis(dithiolene) complex is reacted with the polar solvent, which in this example contains a tert-amine (e.g., dimethylformamide (DMF) and N-methyl-2-pyrrolidone). The tert-amine reduces the nickel bis(dithiolene) complex via an electron transfer reaction to yield the monoionic form of the nickel bis(dithiolene) complex illustrated in the redox reaction in III.

easily formulated into (i.e., dissolved or dispersed rather than precipitated out of) the liquid vehicle at room temperature (e.g., from about 18° C. to about 25° C.) and within a few seconds (e.g., less than 10 seconds), when a thiol surfactant is included in the liquid vehicle.

An example of the thiol surfactant is dodecanethiol, 1-undecanethiol, 2-ethylhexanethiol, 1-octanethiol, 1-tetradecanethiol, and combinations thereof.

The thiol surfactant may be present in the fusing agent in an amount sufficient to stabilize the metal bis(dithiolene) salt components. In an example, the amount of the thiol surfactant in the fusing agent may range from about 1 wt % to about 5 wt % based on the total weight of the fusing agent.

As mentioned above, the polar aprotic solvent may be included in the fusing agent to shift the absorption of the metal bis(dithiolene) salt. In some instances, the shift is further into the NIR region, e.g., shifting from an absorption maximum of about 850 nm to an absorption maximum of about 940 nm when the bis(dithiolene) moiety of the salt is reduced to its subcomponents (e.g., to its monoanionic form or to its dianionic form) according to equation IV.

(IV)

This reduction may be due to the reducing nature of the polar aprotic solvent. As such, in the examples disclosed herein, the polar aprotic solvent is capable of reducing the metal bis(dithiolene) component of the salt to its monoanionic form or to its dianionic form. The polar aprotic solvent may shift the absorption maximum of the metal bis(dithiolene) salt by stabilizing the metal bis(dithiolene) salt components and subcomponents of the reduced metal bis(dithiolene) anion (i.e., monoanionic or dianionic forms).

(III)

Second, the monoionic nickel bis(dithiolene) that is generated is reacted with the nitrogen base. In an example, tetraethylammonium bromide may be used as the nitrogen base. The salt thus formed (generic structure in I) crystallizes out of solution, and can be recovered therefrom.

Whether the salt is purchased or prepared in accordance with the first or second methods disclosed herein, the salt may be incorporated into the liquid vehicle to form the fusing agent. An example of the method for making the fusing agent includes adding a metal bis(dithiolene) salt into a liquid vehicle including at least a polar aprotic solvent and water.

The polar aprotic solvent and water of the liquid vehicle are selected, in part, because the metal bis(dithiolene) salt is soluble therein, with minimal tendency to precipitate out of the liquid vehicle. The metal bis(dithiolene) salt may be The breakdown of the anionic metal bis(dithiolene) moiety to its sub-ionic forms may shift the absorption maximum of the metal bis(dithiolene) salt up to about 100 nm, depending, in part, upon the solvent that is used. For example, 1-methyl-2-pyrrolidone may shift the absorption maximum to about 925 nm, and a 94 nm shift in the absorption maximum may be observed when switching from toluene to DMF. When the metal bis(dithiolene) salt is dissolved, the color of the metal bis(dithiolene) salt may change. For example, the initial reduction of a nickel bis(dithiolene) salt may result in the color changing from reddish brown toward the at least substantially colorless form. However, as described below, water in the liquid vehicle may prevent (further) reduction of the metal bis(dithiolene) anion component in the fusing agent until the water is driven off, and thus the fusing agent may maintain the reddish brown color.

Other color changes may be observed with different metals in the salt. As noted above, the salt can still absorb infrared radiation, and becomes at least substantially colorless during the application of the electromagnetic radiation.

In some examples, the polar aprotic solvent in the liquid vehicle is a polar aprotic solvent containing a tert-amine. In other examples, the polar aprotic solvent is a polar aprotic solvent containing a sec-amine or a tert-amine. In still other examples, the polar aprotic solvent is an organosulfur, an ether, or a ketone. Some specific examples of the polar aprotic solvent include 1-methyl-2-pyrrolidone (1M2P), 2-pyrrolidone, 1-(2-hydroxyethyl)-2-pyrrolidone, dimethylformamide (DMF), dimethyl sulfoxide (DMSO), and combinations thereof.

The polar aprotic solvent is present in the fusing agent in an amount sufficient to maintain the metal bis(dithiolene) salt in solution, and the anionic metal bis(dithiolene) moiety in its monoanionic form or to its dianionic form. In an example, the amount of the polar aprotic solvent in the fusing agent may range from about 5 wt % to about 50 wt % based on the total weight of the fusing agent. In another example, the amount of the polar aprotic solvent present in the fusing agent is about 40 wt % based on the total weight of the fusing agent. In still another example, the amount of the polar aprotic solvent present in the fusing agent is about 50 wt % based on the total weight of the fusing agent.

The liquid vehicle may include water and the polar aprotic solvent, alone or in combination with a mixture of a variety of additional components. One example liquid vehicle consists of water and the polar aprotic solvent (without any other components). When additional components are included, examples of these additional components may include water soluble organic solvent(s), wetting agent(s), surface tension reduction agent(s), emulsifier(s), scale inhibitor(s), anti-deceleration agent(s), chelating agent(s), and/or antimicrobial agent(s).

As mentioned above, the water in the liquid vehicle may prevent (further) reduction of the metal bis(dithiolene) anion component until the water is driven off as a result of the build material platform temperature and/or the temperature achieved during radiation exposure. After the water is driven off, the metal bis(dithiolene) anion component is capable of being further reduced and becoming colorless/discolored, which enables the 3D part to exhibit a color of the build material (e.g., white or off-white) or to exhibit a color of a colorant present in the fusing agent.

The aqueous nature of the fusing agent enables the fusing agent to penetrate, at least partially, into the void spaces of the layer of the polymeric or polymeric composite build material particles. The build material particles may be hydrophobic, and the presence of the wetting agent(s) in the fusing agent may assist in obtaining a particular wetting behavior.

Examples of suitable wetting agents include non-ionic surfactants. Some specific examples include a self-emulsifiable, non-ionic wetting agent based on acetylenic diol chemistry (e.g., SURFYNOL® SEF from Air Products and Chemicals, Inc.), a non-ionic fluorosurfactant (e.g., CAPSTONE® fluorosurfactants from DuPont, previously known as ZONYL FSO), and combinations thereof. In other examples, the wetting agent is an ethoxylated low-foam wetting agent (e.g., SURFYNOL® 440 or SURFYNOL® CT-111 from Air Products and Chemical Inc.) or an ethoxylated wetting agent and molecular defoamer (e.g., SURFYNOL® 420 from Air Products and Chemical Inc.). Still other suitable wetting agents include non-ionic wetting agents and molecular defoamers (e.g., SURFYNOL® 104E from Air Products and Chemical Inc.) or water-soluble, non-ionic surfactants (e.g., TERGITOL™ TMN-6, TERGITOL™ 15S7, and TERGITOL™ 15S9 from The Dow Chemical Company). In some examples, an anionic surfactant may be used in combination with the non-ionic surfactant. In some examples, it may be desirable to utilize a wetting agent having a hydrophilic-lipophilic balance (HLB) less than 10.

The wetting agent(s) may be present in the fusing agent in an amount ranging from about 0.04 wt % to about 4 wt % of the total weight of the fusing agent. In an example, the amount of the wetting agent(s) present in the fusing agent is about 0.1 wt % (based on the total weight of the fusing agent). In another example, the amount of the wetting agent(s) present in the fusing agent is about 0.04 wt % (based on the total weight of the fusing agent).

The liquid vehicle may also include surface tension reduction agent(s). Any of the previously mentioned wetting agents/surfactants may be used to reduce the surface tension. As an example, the surface tension reduction agent may be the self-emulsifiable, non-ionic wetting agent based on acetylenic diol chemistry (e.g., SURFYNOL® SEF from Air Products and Chemicals, Inc.).

The surface tension reduction agent(s) may be present in the fusing agent in an amount ranging from about 0.1 wt % to about 4 wt % of the total weight of the fusing agent. In an example, the amount of the surface tension reduction agent(s) present in the fusing agent is about 1.5 wt % (based on the total weight of the fusing agent). In another example, the amount of the surface tension reduction agent(s) present in the fusing agent is about 0.6 wt % (based on the total weight of the fusing agent).

When a surfactant is both a wetting agent and a surface tension reduction agent, any of the ranges presented herein for the wetting agent and the surface tension reduction agent may be used for the surfactant.

The liquid vehicle may also include water soluble organic solvent(s). In some examples, the water soluble organic solvent(s) may be the same type of solvent as the polar aprotic solvent. In these examples, the water soluble organic solvent(s) may be 1-methyl-2-pyrrolidone (1M2P), 2-pyrrolidone, 1-(2-hydroxyethyl)-2-pyrrolidone, dimethylformamide (DMF), dimethyl sulfoxide (DMSO), or a combination thereof. In other examples, the water soluble organic solvent(s) may be different than the polar aprotic solvent. For example, two different polar aprotic solvents may be selected. For another example, the water soluble organic solvent(s) may be 1,5-pentanediol, pentanol, triethylene glycol, tetraethylene glycol, 2-methyl-1,3-propanediol, 1,6-hexanediol, tripropylene glycol methyl ether, or a combination thereof.

The water soluble organic solvent(s) may be present in the fusing agent in an amount ranging from about 2 wt % to about 80 wt % of the total weight of the fusing agent. In an example, the amount of the water soluble organic solvent(s) present in the fusing agent is about 40 wt % (based on the total weight of the fusing agent). In another example, the amount of the water soluble organic solvent(s) present in the fusing agent is about 16 wt % (based on the total weight of the fusing agent).

The liquid vehicle may also include emulsifier(s). Examples of suitable emulsifiers include oleth-3-phosphate (commercially available as CRODAFOS™ O3A or CRODAFOS™ N-3 acid) or dextran 500 k. Other suitable examples of the emulsifiers include CRODAFOS™ HCE (phosphate-ester from Croda Int.), CRODAFOS® N10 (oleth-10-phosphate from Croda Int.), etc.

The emulsifier(s) may be present in the fusing agent in an amount ranging from about 0.1 wt % to about 2 wt % of the total weight of the fusing agent. In an example, the amount of the emulsifier(s) present in the fusing agent is about 1 wt % (based on the total weight of the fusing agent). In another example, the amount of the emulsifier(s) present in the fusing agent is about 0.4 wt % (based on the total weight of the fusing agent).

The fusing agent may include scale inhibitor(s) or anti-deceleration agent(s). One suitable scale inhibitor/anti-deceleration agent is an alkyldiphenyloxide disulfonate (e.g., DOWFAX™ 8390 and DOWFAX™ 2A1 from The Dow Chemical Company).

The scale inhibitor(s)/anti-deceleration agent(s) may be present in the fusing agent in an amount ranging from about 0.05 wt % to about 5 wt % of the total weight of the fusing agent. In an example, the scale inhibitor(s)/anti-deceleration agent(s) is/are present in the fusing agent in an amount of about 0.25 wt % (based on the total weight of the fusing agent). In another example, the scale inhibitor(s)/anti-deceleration agent(s) is/are present in the fusing agent in an amount of about 0.1 wt % (based on the total weight of the fusing agent).

The fusing agent may also include chelating agent(s). The chelating agent may be included to eliminate the deleterious effects of heavy metal impurities. Examples of suitable chelating agents include disodium ethylenediaminetetraacetic acid (EDTA-Na), ethylenediaminetetraacetic acid (EDTA), and methylglycinediacetic acid (e.g., TRILON® M from BASF Corp.).

Whether a single chelating agent is used or a combination of chelating agents is used, the total amount of chelating agent(s) in the fusing agent may range from 0 wt % to about 2 wt % based on the total weight of the fusing agent. In an example, the chelating agent is present in the fusing agent in an amount of about 0.08 wt % (based on the total weight of the fusing agent). In another example, the chelating agent is present in the fusing agent in an amount of about 0.032 wt % (based on the total weight of the fusing agent).

The liquid vehicle may also include antimicrobial agent(s). Suitable antimicrobial agents include biocides and fungicides. Example antimicrobial agents may include the NUOSEPT® (Ashland Inc.), UCARCIDE™ or KORDEK™ (Dow Chemical Co.), and PROXEL® (Arch Chemicals) series, ACTICIDE® M20 (Thor), and combinations thereof.

In an example, the fusing agent may include a total amount of antimicrobial agents that ranges from about 0.1 wt % to about 0.35 wt %. In an example, the antimicrobial agent is a biocide and is present in the fusing agent in an amount of about 0.32 wt % (based on the total weight of the fusing agent). In another example, the antimicrobial agent is a biocide and is present in the fusing agent in an amount of about 0.128 wt % (based on the total weight of the fusing agent).

The balance of the fusing agent is water. As an example, deionized water may be used.

In an example, the fusing agent includes from about 1 wt % to about 3 wt % of the metal bis(dithiolene) salt, from about 5 wt % to about 50 wt % of the polar aprotic solvent, and a balance of water (based on the total weight of the fusing agent).

In another example, the fusing agent includes from about 1 wt % to about 3 wt % of the metal bis(dithiolene) salt, from about 1 wt % to about 5 wt % of the thiol surfactant, from about 5 wt % to about 50 wt % of the polar aprotic solvent, and a balance of water (based on the total weight of the fusing agent).

In some examples the fusing agent may include a colorant in addition to the metal bis(dithiolene) salt. While the metal bis(dithiolene) salt functions as an electromagnetic radiation absorber and becomes colorless after fusing the build material, the additional colorant may impart color to the fusing agent and the resulting 3D part. The amount of the colorant that may be present in the fusing agent ranges from about 1 wt % to about 10 wt % based on the total weight of the fusing agent. The colorant may be a pigment and/or dye having any suitable color. Examples of the colors include cyan, magenta, yellow, etc. Examples of colorants include dyes, such as Acid Yellow 23 (AY 23), Acid Yellow 17 (AY 17), Acid Red 52 (AR 52), Acid Red 289 (AR 289), Reactive Red 180 (RR 180), Direct Blue 199 (DB 199), or pigments, such as Pigment Blue 15:3 (PB 15:3), Pigment Red 122 (PR 122), Pigment Yellow 155 (PY 155), and Pigment Yellow 74 (PY 74).

In some other examples, the fusing agent excludes a colorant other than the metal bis(dithiolene) salt. It may be desirable to exclude the colorant from the fusing agent when the 3D part to be created is to be the color of the polymeric or polymeric composite build material (e.g., white or off-white) or when a colored ink will be applied to the 3D part.

Figure 1:
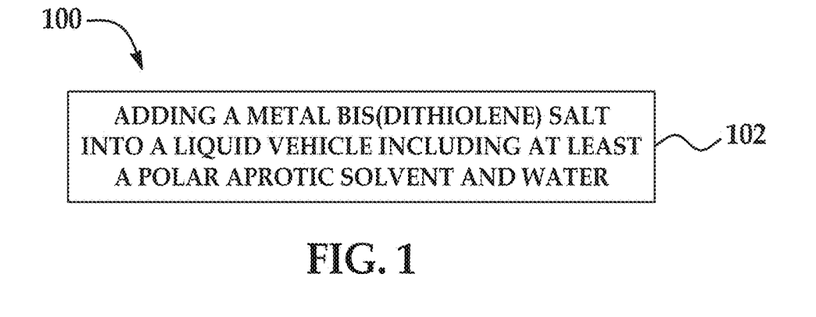
FIG. 1 is a diagram illustrating an example of a method of making an example of the fusing agent disclosed herein.

Also disclosed herein is a method of making the fusing agent. An example of this method 100 is shown in FIG. 1. As shown at reference numeral 102 of FIG. 1, the method 100 includes adding a metal bis(dithiolene) salt into a liquid vehicle including at least a polar aprotic solvent and water. In an example, the fusing agent may be prepared by exposing a metal bis(dithiolene) salt to a solution including a polar aprotic solvent, thereby dissolving the metal bis(dithiolene) salt in the solution to form the cation and anion of the metal bis(dithiolene). The anionic metal bis(dithiolelene) is further reduced to the metal and monoanionic or dianionic moieties due to the reducing nature of the polar aprotic solvent.

An example of the method 100 further includes incorporating into the liquid vehicle a water soluble organic solvent and an additive selected from the group consisting of an emulsifier, a surface tension reduction agent, a wetting agent, a scale inhibitor, an anti-deceleration agent, a chelating agent, an antimicrobial agent, and a combination thereof.

In some examples, the metal bis(dithiolene) salt is exposed to the liquid vehicle at room temperature (e.g., a temperature ranging from about 18° C. to about 25° C. The metal bis(dithiolene) salt may be dissolved and reduced in the liquid vehicle within few seconds (e.g., less than 10 seconds).

It is to be understood that the metal bis(dithiolene) salt, the polar aprotic solvent, and the additive(s) may be any of the examples and may be included in any of the amounts described above.

Figure 2:
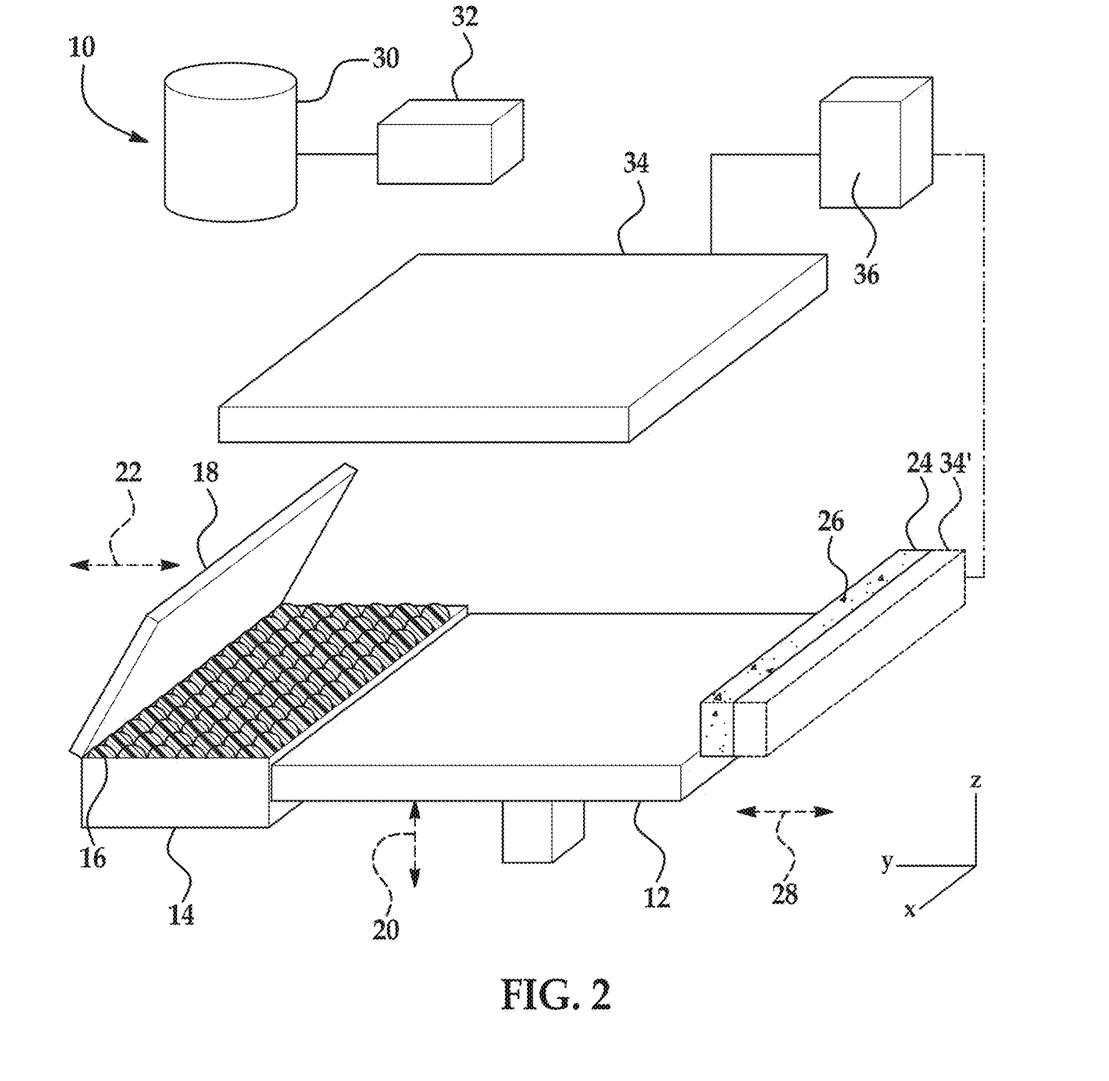
FIG. 2 is a simplified isometric and schematic view of an example of a 3D printing system disclosed herein.

Referring now to FIG. 2, an example of a 3D printing system 10 is schematically depicted. It is to be understood that the 3D printing system 10 may include additional components and that some of the components described herein may be removed and/or modified. Furthermore, components of the 3D printing system 10 depicted in FIG. 2 may not be drawn to scale and thus, the 3D printing system 10 may have a different size and/or configuration other than as shown therein.

Figure 3A:
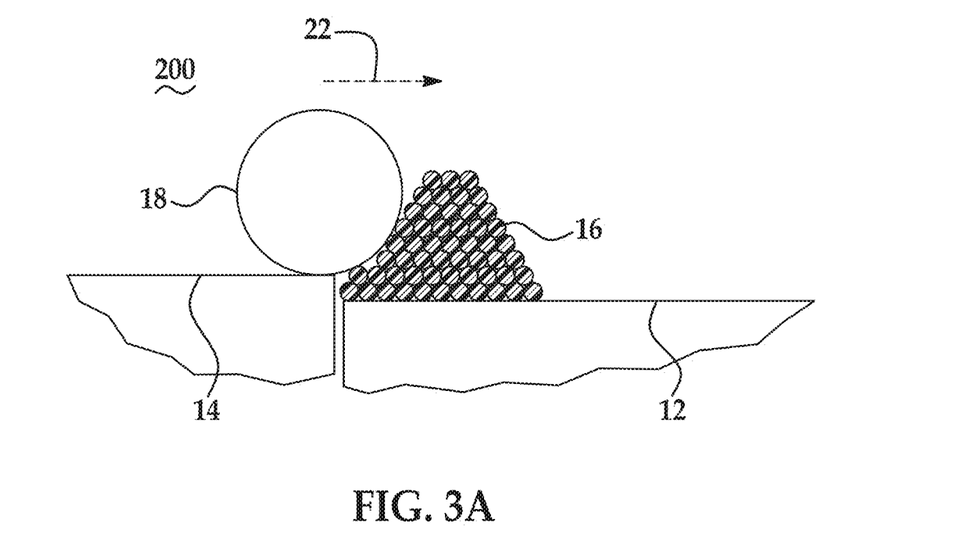
FIGS. 3A through 3D are schematic and partially cross-sectional views depicting the formation of a 3D part using examples of a 3D printing method disclosed herein.
Figure 3B:
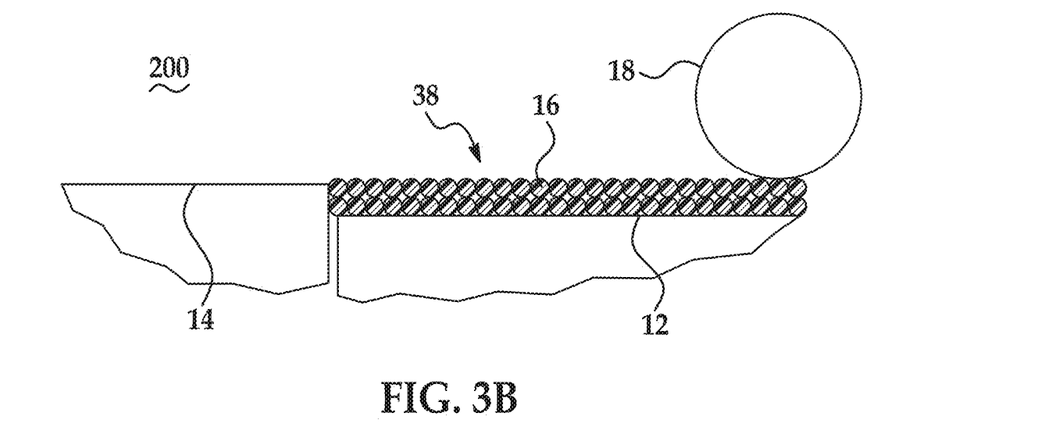
Figure 3C:
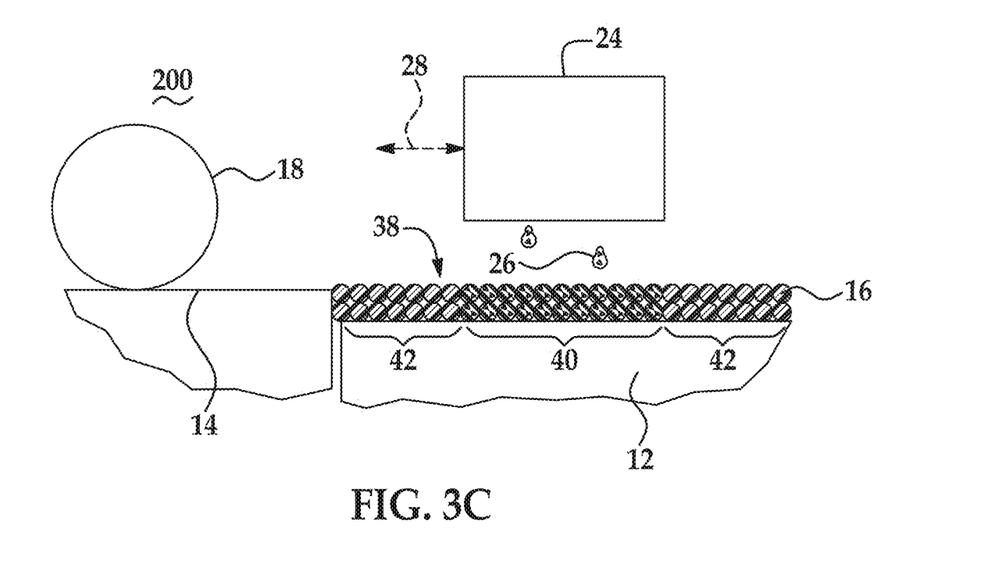
Figure 3D:
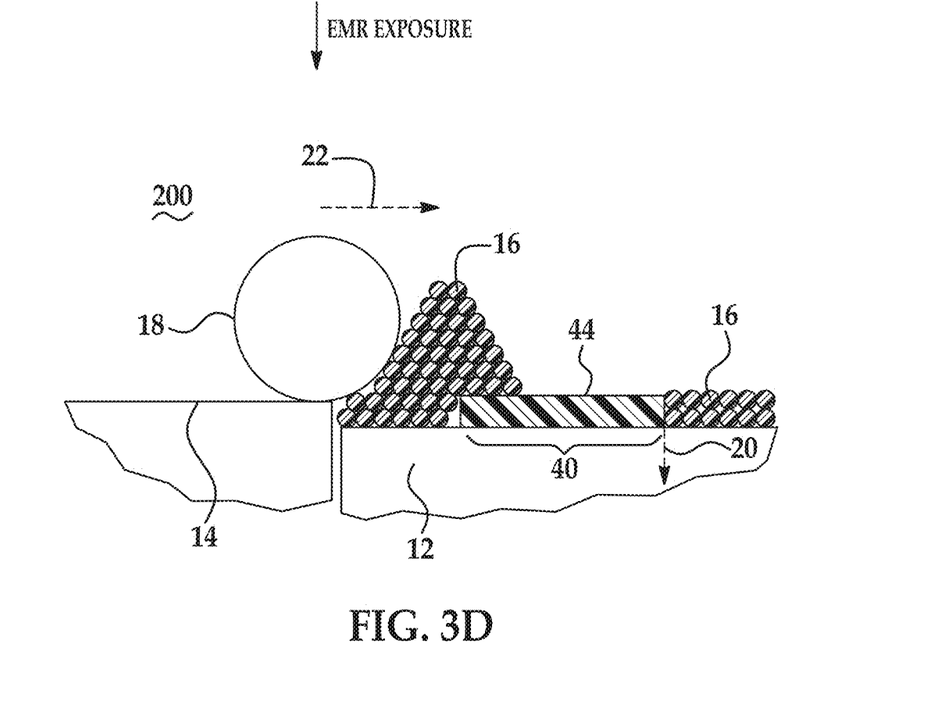

In an example, the three-dimensional (3D) printing system includes a supply 14 of polymeric or polymeric composite build material 16; a build material distributor 18; a supply of a fusing agent 26, the fusing agent 26 including:

a metal bis(dithiolene) salt; a polar aprotic solvent; and a balance of water; an applicator 24 for selectively dispensing the fusing agent 26; a source 34, 34' of electromagnetic radiation; a controller 30; and a non-transitory computer readable medium having stored thereon computer executable instructions to cause the controller to: utilize the build material distributor 18 to dispense the polymeric or polymeric composite build material 16; utilize the applicator 24 to selectively dispense the fusing agent 26 on at least a portion of the polymeric or polymeric composite build material 16; and utilize the source 34, 34' of electromagnetic radiation to expose the polymeric or polymeric composite build material 16 to electromagnetic radiation, thereby fusing the portion of the polymeric or polymeric composite build material 16 in contact with the fusing agent 26 to form a layer 44 (see FIG. 3D).

As mentioned, the printing system 10 includes the build area platform 12, the build material supply 14 containing polymeric or polymeric composite build material particles 16, and the build material distributor 18.

The build area platform 12 receives the polymeric or polymeric composite build material 16 from the build material supply 14. The build area platform 12 may be integrated with the printing system 10 or may be a component that is separately insertable into the printing system 10. For example, the build area platform 12 may be a module that is available separately from the printing system 10. The build material platform 12 that is shown is also one example, and could be replaced with another support member, such as a platen, a fabrication/print bed, a glass plate, or another build surface.

The build area platform 12 may be moved in a direction as denoted by the arrow 20, e.g., along the z-axis, so that polymeric or polymeric composite build material 16 may be delivered to the platform 12 or to a previously formed layer of the 3D part. In an example, when the polymeric or polymeric composite build material particles 16 are to be delivered, the build area platform 12 may be programmed to advance (e.g., downward) enough so that the build material distributor 18 can push the polymeric or polymeric composite build material particles 16 onto the platform 12 to form a substantially uniform layer of the polymeric or polymeric composite build material 16 thereon (see, e.g., FIGS. 2A and 2B). The build area platform 12 may also be returned to its original position, for example, when a new part is to be built.

The build material supply 14 may be a container, bed, or other surface that is to position the polymeric or polymeric composite build material particles 16 between the build material distributor 18 and the build area platform 12. In some examples, the build material supply 14 may include a surface upon which the polymeric or polymeric composite build material particles 16 may be supplied, for instance, from a build material source (not shown) located above the build material supply 14. Examples of the build material source may include a hopper, an auger conveyer, or the like. Additionally, or alternatively, the build material supply 14 may include a mechanism (e.g., a delivery piston) to provide, e.g., move, the polymeric or polymeric composite build material particles 16 from a storage location to a position to be spread onto the build area platform 12 or onto a previously formed layer of the 3D part.

The build material distributor 18 may be moved in a direction as denoted by the arrow 22, e.g., along the y-axis, over the build material supply 14 and across the build area platform 12 to spread a layer of the polymeric or polymeric composite build material 16 over the build area platform 12. The build material distributor 18 may also be returned to a position adjacent to the build material supply 14 following the spreading of the polymeric or polymeric composite build material particles 16. The build material distributor 18 may be a blade (e.g., a doctor blade), a roller, a combination of a roller and a blade, and/or any other device capable of spreading the polymeric or polymeric composite build material 16 over the build area platform 12. For instance, the build material distributor 18 may be a counter-rotating roller.

The polymeric or polymeric composite build material particles 16 may be a polymeric build material or a polymeric composite build material. As used herein, the term "polymeric build material" may refer to crystalline or semi-crystalline polymer particles. As used herein, the term "polymeric composite build material" may refer or composite particles made up of polymer and ceramic. Any of the polymeric or polymeric composite build material particles 16 may be in powder form.

Examples of semi-crystalline polymers include semi-crystalline thermoplastic materials with a wide processing window of greater than 5° C. (i.e., the temperature range between the melting point and the re-crystallization temperature). Some specific examples of the semi-crystalline thermoplastic materials include polyamides (PAs) (e.g., PA 11/nylon 11, PA 12/nylon 12, PA 6/nylon 6, PA 8/nylon 8, PA 9/nylon 9, PA 66/nylon 66, PA 612/nylon 612, PA 812/nylon 812, PA 912/nylon 912, etc.). Other examples of crystalline or semi-crystalline polymers suitable for use as the build material particles 16 include polyethylene, polypropylene, and polyoxomethylene (i.e., polyacetals). Still other examples of suitable build material particles 16 include polystyrene, polycarbonate, polyester, polyurethanes, other engineering plastics, and blends of any two or more of the polymers listed herein.

Any of the previously listed crystalline or semi-crystalline polymer particles may be combined with ceramic particles to form the polymeric composite build material particles 16. Examples of suitable ceramic particles include metal oxides, inorganic glasses, carbides, nitrides, and borides. Some specific examples include alumina ($Al_2O_3$), glass, silicon mononitride (SiN), silicon dioxide ($SiO_2$), zirconia ($ZrO_2$), titanium dioxide ($TiO_2$), or combinations thereof. The amount of ceramic particles that may be combined with the crystalline or semi-crystalline polymer particles may depend on the materials used and the 3D part to be formed. In one example, the ceramic particles may be present in an amount ranging from about 1 wt % to about 20 wt % based on the total weight of the polymeric composite build material particles 16.

The polymeric or polymeric composite build material particles 16 may have a melting point or softening point ranging from about 50° C. to about 400° C. As an example, the build material particles 16 may be a polyamide having a melting point of 180° C.

The polymeric or polymeric composite build material particles 16 may be made up of similarly sized particles or differently sized particles. The term "size", as used herein with regard to the polymeric or polymeric composite build material particles 16, refers to the diameter of a spherical particle, or the average diameter of a non-spherical particle (i.e., the average of multiple diameters across the particle), or the volume-weighted mean diameter of a particle distribution. In an example, the average size of the polymeric or polymeric composite build material particles 16 ranges from 5 μm to about 200 μm.

It is to be understood that the polymeric or polymeric composite build material 16 may include, in addition to polymeric or polymeric composite particles, a charging agent, a flow aid, or combinations thereof.

Charging agent(s) may be added to suppress tribo-charging. Examples of suitable charging agent(s) include aliphatic amines (which may be ethoxylated), aliphatic amides, quaternary ammonium salts (e.g., behentrimonium chloride or cocamidopropyl betaine), esters of phosphoric acid, polyethylene glycolesters, or polyols. Some suitable commercially available charging agents include HOSTASTAT® FA 38 (natural based ethoxylated alkylamine), HOSTASTAT® FE2 (fatty acid ester), and HOSTASTAT® HS 1 (alkane sulfonate), each of which is available from Clariant Int. Ltd.). In an example, the charging agent is added in an amount ranging from greater than 0 wt % to less than 5 wt % based upon the total weight of the polymeric or polymeric composite build material 16.

Flow aid(s) may be added to improve the coating flowability of the polymeric or polymeric composite build material 16. Flow aid(s) may be particularly beneficial when the particles of the polymeric or polymeric composite build material 16 are less than 25 µm in size. The flow aid improves the flowability of the polymeric or polymeric composite build material 16 by reducing the friction, the lateral drag, and the tribocharge buildup (by increasing the particle conductivity). Examples of suitable flow aids include tricalcium phosphate (E341), powdered cellulose (E460(ii)), magnesium stearate (E470b), sodium bicarbonate (E500), sodium ferrocyanide (E535), potassium ferrocyanide (E536), calcium ferrocyanide (E538), bone phosphate (E542), sodium silicate (E550), silicon dioxide (E551), calcium silicate (E552), magnesium trisilicate (E553a), talcum powder (E553b), sodium aluminosilicate (E554), potassium aluminum silicate (E555), calcium aluminosilicate (E556), bentonite (E558), aluminum silicate (E559), stearic acid (E570), or polydimethylsiloxane (E900). In an example, the flow aid is added in an amount ranging from greater than 0 wt % to less than 5 wt % based upon the total weight of the polymeric or polymeric composite build material 16.

As shown in FIG. 2, the printing system 10 also includes an applicator 24, which may contain the fusing agent 26 disclosed herein.

As mentioned above, the fusing agent 26 may include the metal bis(dithiolene) salt and the liquid vehicle. In an example, the fusing agent 26 includes the metal bis(dithiolene) salt, the thiol surfactant, the polar aprotic solvent, and a balance of water. In another example, the fusing agent 26 consists of these components and no other components. In still another example, the fusing agent 26 includes from about 1 wt % to about 3 wt % of the metal bis(dithiolene) salt, from about 1 wt % to about 5 wt % of the thiol surfactant, from about 5 wt % to about 50 wt % of the polar aprotic solvent, and a balance of water (based on the total weight of the fusing agent 26). As also mentioned above, in some examples, the fusing agent 26 includes the colorant. In an example, the fusing agent 26 consists of the metal bis(dithiolene) salt, the thiol surfactant, the polar aprotic solvent, the colorant, and a balance of water. In still other examples, the fusing agent 26 excludes the colorant.

The applicator 24 may be scanned across the build area platform 12 in the direction indicated by the arrow 28, e.g., along the y-axis. The applicator 24 may be, for instance, a thermal inkjet printhead, a piezoelectric printhead, a continuous inkjet printhead, etc., and may extend a width of the build area platform 12. While the applicator 24 is shown in FIG. 2 as a single applicator, it is to be understood that the applicator 24 may include multiple applicators that span the width of the build area platform 12. Additionally, the applicators 24 may be positioned in multiple printbars. The applicator 24 may also be scanned along the x-axis, for instance, in configurations in which the applicator 24 does not span the width of the build area platform 12 to enable the applicator 24 to deposit the fusing agent 26 over a large area of a layer of polymeric or polymeric composite build material particles 16. The applicator 24 may thus be attached to a moving XY stage or a translational carriage (neither of which is shown) that moves the applicator 24 adjacent to the build area platform 12 in order to deposit the fusing agent 26 in predetermined areas of a layer of the polymeric or polymeric composite build material particles 16 that has been formed on the build area platform 12 in accordance with the method(s) disclosed herein. The applicator 24 may include a plurality of nozzles (not shown) through which the fusing agent 26 is to be ejected.

The applicator 24 may deliver drops of the fusing agent 26 at a resolution ranging from about 300 dots per inch (DPI) to about 1200 DPI. In other examples, the applicator 24 may deliver drops of the fusing agent 26 at a higher or lower resolution. The drop velocity may range from about 5 m/s to about 24 m/s, and the firing frequency may range from about 1 kHz to about 100 kHz. In one example, the volume of each drop may be on the order of about 3 picoliters (pl) to about 18 pl, although it is contemplated that a higher or lower drop volume may be used. In some examples, the inkjet applicator 24 is able to deliver variable drop volumes of the binder fluid 36.

In some examples of the system 10 disclosed herein, another applicator (not shown) may be included that is capable of applying a colored ink to the 3D part that is formed. This applicator may be similar to or the same as applicator 24. It may be desirable to include this applicator and the colored ink when the 3D part is the color of the polymeric or polymeric composite build material (e.g., white or off-white), and when it is desirable to apply color to the white or off-white 3D part.

An example of a pigment based colored ink may include from about 1 wt % to about 10 wt % of pigment(s), from about 10 wt % to about 30 wt % of co-solvent(s), from about 0.5 wt % to about 2 wt % of dispersant(s), from 0.01 wt % to about 1 wt % of anti-kogation agent(s), from about 0.1 wt % to about 5 wt % of binder(s), from about 0.05 wt % to about 0.1 wt % biocide(s), and a balance of water. An example of a dye based colored ink may include from about 1 wt % to about 7 wt % of dye(s), from about 10 wt % to about 30 wt % of co-solvent(s), from about 0.25 wt % to about 2 wt % of dispersant(s), from 0.05 wt % to about 0.1 wt % of chelating agent(s), from about 0.005 wt % to about 0.2 wt % of buffer(s), from about 0.05 wt % to about 0.1 wt % biocide(s), and a balance of water. Some specific examples of suitable colored inks include a set of cyan, magenta, and yellow inks, such as C1893A (cyan), C1984A (magenta), and C1985A (yellow); or C4801A (cyan), C4802A (magenta), and C4803A (yellow); all of which are available from HP Inc. Other commercially available colored inks include C9384A (printhead HP 72), C9383A (printhead HP 72), C4901A (printhead HP 940), and C4900A (printhead HP 940).

Each of the previously described physical elements of the system 10 may be operatively connected to a controller 30 of the printing system 10. The controller 30 may control the operations of the build area platform 12, the build material supply 14, the build material distributor 18, and the applicator 24. As an example, the controller 30 may control actuators (not shown) to control various operations of the 3D printing system 10 components. The controller 30 may be a computing device, a semiconductor-based microprocessor, a central processing unit (CPU), an application specific integrated circuit (ASIC), and/or another hardware device. Although not shown, the controller 30 may be connected to the 3D printing system 10 components via communication lines.

The controller 30 manipulates and transforms data, which may be represented as physical (electronic) quantities within the printer's registers and memories, in order to control the physical elements to create the 3D part. As such, the controller 30 is depicted as being in communication with a data store 32. The data store 32 may include data pertaining to a 3D part to be printed by the 3D printing system 10. The data for the selective delivery of the polymeric or polymeric composite build material particles 16, the fusing agent 26, etc. may be derived from a 3D object model of the 3D part to be formed. For instance, the data may include the locations on each layer of polymeric or polymer composite build material particles 16 that the applicator 24 is to deposit the fusing agent 26. In one example, the controller 30 may use the data to control the applicator 24 to selectively apply the fusing agent 26. The data store 32 may also include machine readable instructions (stored on a non-transitory computer readable medium) that are to cause the controller 30 to control the amount of polymeric or polymeric composite build material particles 16 that is supplied by the build material supply 14, the movement of the build area platform 12, the movement of the build material distributor 18, the movement of the applicator 24, etc.

As shown in FIG. 2, the printing system 10 may also include a source of electromagnetic radiation 34, 34'. In some examples, the source of electromagnetic radiation 34, 34' may be in a fixed position with respect to the build material platform 12. In other examples, the source of electromagnetic radiation 34, 34' may be positioned to expose the layer of polymeric or polymeric composite build material particles 16 to electromagnetic radiation immediately after the fusing agent 26 has been applied thereto. In the example shown in FIG. 2, the source of electromagnetic radiation 34' is attached to the side of the applicator 24 which allows for patterning and heating in a single pass.

The source of electromagnetic radiation 34, 34' may emit electromagnetic radiation having wavelengths ranging from about 800 nm to about 1 mm. As one example, the electromagnetic radiation may range from about 800 nm to about 2 μm. As another example, the electromagnetic radiation may be blackbody radiation with a maximum intensity at a wavelength of about 1100 nm. The source of electromagnetic radiation 34, 34' may be infrared (IR) or near-infrared light sources, such as IR or near-IR curing lamps, IR or near-IR light emitting diodes (LED), or lasers with the desirable IR or near-IR electromagnetic wavelengths.

The source of electromagnetic radiation 34, 34' may be operatively connected to a lamp/laser driver, an input/output temperature controller, and temperature sensors, which are collectively shown as radiation system components 36. The radiation system components 36 may operate together to control the source of electromagnetic radiation 34, 34'. The temperature recipe (e.g., radiation exposure rate) may be submitted to the input/output temperature controller. During heating, the temperature sensors may sense the temperature of the polymeric or polymeric composite build material particles 16, and the temperature measurements may be transmitted to the input/output temperature controller. For example, a thermometer associated with the heated area can provide temperature feedback. The input/output temperature controller may adjust the source of electromagnetic radiation 34, 34' power set points based on any difference between the recipe and the real-time measurements. These power set points are sent to the lamp/laser drivers, which transmit appropriate lamp/laser voltages to the source of electromagnetic radiation 34, 34'. This is one example of the radiation system components 36, and it is to be understood that other radiation source control systems may be used. For example, the controller 30 may be configured to control the source of electromagnetic radiation 34, 34'.

Referring now to FIGS. 3A through 3D, an example of the 3D printing method 200 is depicted. This method 200 may be used to form 3D printed parts having mechanical integrity (e.g., having an ultimate tensile strength ranging from about 40 MPa to about 55 MPa and being white, off-white, or colored. In other examples, the ultimate tensile strength of the 3D printed part may range from about 40 MPa to about 51 MPa or from about 40 MPa to about 45 MPa.

Prior to execution of the method 200 or as part of the method 200, the controller 30 may access data stored in the data store 32 pertaining to a 3D part that is to be printed. The controller 30 may determine the number of layers of polymeric or polymeric composite build material 16 that are to be formed, and the locations at which the fusing agent 26 from the applicator 24 is to be deposited on each of the respective layers.

As shown in FIGS. 3A and 3B, the method 200 includes applying the polymeric or polymeric composite build material 16. In FIG. 3A, the build material supply 14 may supply the polymeric or polymeric composite build material particles 16 into a position so that they are ready to be spread onto the build area platform 12. In FIG. 3B, the build material distributor 18 may spread the supplied polymeric or polymeric composite build material particles 16 onto the build area platform 12. The controller 30 may execute control build material supply instructions to control the build material supply 14 to appropriately position the polymeric or polymeric composite build material particles 16, and may execute control spreader instructions to control the build material distributor 18 to spread the supplied polymeric or polymeric composite build material particles 16 over the build area platform 12 to form a layer 38 of polymeric or polymeric composite build material particles 16 thereon. As shown in FIG. 3B, one layer 38 of the polymeric or polymeric composite build material particles 16 has been applied.

The layer 38 has a substantially uniform thickness across the build area platform 12. In an example, the thickness of the layer 38 ranges from about 50 μm to about 300 μm, although thinner or thicker layers may also be used. For example, the thickness of the layer 38 may range from about 20 μm to about 500 μm, or from about 30 μm to about 300 μm. The layer thickness may be about 2× the particle diameter (as shown in FIG. 3B) at a minimum for finer part definition.

Prior to further processing, the layer 38 of the polymeric or polymeric composite build material particles 16 may be exposed to heating. Heating may be performed to pre-heat the polymeric or polymeric composite build material particles 16, and thus the heating temperature may be below the melting point or softening point of the polymeric or polymeric composite build material particles 16. As such, the temperature selected will depend upon the polymeric or polymeric composite build material particles 16 that are used. As examples, the pre-heating temperature may be from about 5° C. to about 50° C. below the melting point or softening point of the polymeric or polymeric composite build material particles 16. In an example, the pre-heating temperature ranges from about 50° C. to about 350° C. In another example, the pre-heating temperature ranges from about 150° C. to about 170° C.

Pre-heating the layer 38 of the polymeric or polymeric composite build material particles 16 may be accomplished using any suitable heat source that exposes all of the polymeric or polymeric composite build material particles 16 on the build material surface 12 to the heat. Examples of the heat source include a thermal heat source (e.g., a heater (not shown) of the particles 16) or the electromagnetic radiation source 34, 34'.

Referring now to FIG. 3C, after the layer 38 is formed, and in some instances is pre-heated, the fusing agent 26 is selectively applied on at least a portion 40 of the polymeric or polymeric composite build material 16.

It is to be understood that a single fusing agent 26 may be selectively applied on the portion 40, or multiple fusing agents 26 may be selectively applied on the portion 40. As an example, multiple fusing agents 26 may be used when the colorant is included in at least one of the multiple fusing agents 26 to create a multi-colored part.

As illustrated in FIG. 3C, the fusing agent 26 may be dispensed from the applicator 24. The controller 32 may execute instructions to control the applicator 24 (e.g., in the directions indicated by the arrow 28) to deposit the fusing agent 26 onto predetermined portion(s) 40 of the polymeric or polymeric composite build material 16 that are to become part of the 3D part. The applicator 24 may be programmed to receive commands from the controller 30 and to deposit the fusing agent 26 according to a pattern of a cross-section for the layer of the 3D part to be formed. As used herein, the cross-section of the layer of the 3D part to be formed refers to the cross-section that is parallel to the surface of the build area platform 12. In the example shown in FIG. 3C, the applicator 24 selectively applies the fusing agent 26 on those portion(s) 40 of the layer 38 that are to be fused to become the first layer of the 3D part. As an example, if the 3D part that is to be formed is to be shaped like a cube or cylinder, the fusing agent 26 will be deposited in a square pattern or a circular pattern (from a top view), respectively, on at least a portion of the layer 38 of the polymeric or polymeric composite build material particles 16. In the example shown in FIG. 3C, the fusing agent 26 is deposited in a square pattern on the portion 40 of the layer 38 and not on the portions 42.

As mentioned above, the fusing agent 26 may include the metal bis(dithiolene) salt and the liquid vehicle. In an example, the fusing agent 26 includes the metal bis(dithiolene) salt, the thiol surfactant, the polar aprotic solvent, and a balance of water. In another example, the fusing agent 26 consists of these components and no other components. In still another example, the fusing agent 26 includes from about 1 wt % to about 3 wt % of the metal bis(dithiolene) salt, from about 1 wt % to about 5 wt % of the thiol surfactant, from about 5 wt % to about 50 wt % of the polar aprotic solvent, and a balance of water (based on the total weight of the fusing agent 26). As also mentioned above, in some examples, the fusing agent 26 includes the colorant. In an example, the fusing agent 26 consists of the metal bis(dithiolene) salt, the thiol surfactant, the polar aprotic solvent, the colorant, and a balance of water. In still other examples, the fusing agent 26 excludes the colorant.

The volume of the fusing agent 26 that is applied per unit of the polymeric or polymeric composite build material 16 in the patterned portion 40 may be sufficient to absorb and convert enough electromagnetic radiation so that the polymeric or polymeric composite build material 16 in the patterned portion 40 will fuse. The volume of the fusing agent 26 that is applied per unit of the polymer or polymeric composite build material 16 may depend, at least in part, on the metal bis(dithiolene) salt used, the metal bis(dithiolene) salt loading in the fusing agent 26, and the polymeric or polymeric composite build material 16 used.

As shown between FIGS. 3C and 3D, after applying the fusing agent 26, the entire layer 38 of the polymeric or polymeric composite build material 16 is exposed to electromagnetic radiation (shown as EMR Exposure between FIGS. 3C and 3D).

The electromagnetic radiation is emitted from the source of electromagnetic radiation 34, 34' (shown in FIG. 2). The length of time the electromagnetic radiation is applied for, or energy exposure time, may be dependent, for example, on one or more of: characteristics of the electromagnetic radiation 34, 34'; characteristics of the polymeric or polymeric composite build material particles 16; and/or characteristics of the fusing agent 26.

The fusing agent 26 enhances the absorption of the radiation, converts the absorbed radiation to thermal energy, and promotes the transfer of the thermal heat to the polymeric or polymeric composite build material particles 16 in contact therewith. In an example, the fusing agent 26 sufficiently elevates the temperature of the polymeric or polymeric composite build material particles 16 in layer 38 above the melting or softening point of the particles 16, allowing fusing (e.g., sintering, binding, curing, etc.) of the polymeric or polymeric composite build material particles 16 to take place. Exposure to electromagnetic radiation forms the fused layer 44, as shown in FIG. 3D.

It is to be understood that portions 42 of the polymeric or polymeric composite build material 16 that do not have the fusing agent 26 applied thereto may not absorb enough radiation to fuse. As such, these portions 42 may not become part of the 3D part that is ultimately formed. The polymeric or polymeric composite build material 16 in portions 42 may be reclaimed to be reused as build material in the printing of another 3D part.

The processes shown in FIGS. 3A through 3D may be repeated to iteratively build up several fused layers and to form the 3D printed part. FIG. 3D illustrates the initial formation of a second layer of polymeric or polymeric composite build material particles 16 on the previously formed layer 44. In FIG. 3D, following the fusing of the predetermined portion(s) 40 of the layer 38 of polymeric or polymeric composite build material 16, the controller 30 may execute instructions to cause the build area platform 12 to be moved a relatively small distance in the direction denoted by the arrow 20. In other words, the build area platform 12 may be lowered to enable the next layer of polymeric or polymeric composite build material particles 16 to be formed. For example, the build material platform 12 may be lowered a distance that is equivalent to the height of the layer 38. In addition, following the lowering of the build area platform 12, the controller 30 may control the build material supply 14 to supply additional polymeric or polymeric composite build material particles 16 (e.g., through operation of an elevator, an auger, or the like) and the build material distributor 18 to form another layer of polymeric or polymeric composite build material particles 16 on top of the previously formed layer with the additional polymeric or polymeric composite build material 16. The newly formed layer may be in some instances preheated, patterned with the fusing agent 26, and then exposed to radiation from the source of electromagnetic radiation 34, 34' to form the additional fused layer.

Since the metal bis(dithiolene) anionic moiety may be further reduced at least during fusing, the layer 44 (and the final 3D part) exhibits a color of the build material (e.g., white or off-white) or exhibits a color of a colorant present in the fusing agent 26, due in part to the at least substantially colorless form of the bis(dithiolene) anionic moiety. If it is desirable to impart color to the layer 44, the colored ink may be selectively applied to at least a portion of the layer 44.

To further illustrate the present disclosure, examples are given herein. It is to be understood that these examples are provided for illustrative purposes and are not to be construed as limiting the scope of the present disclosure.

EXAMPLES

Example 1

An example of the salt disclosed herein was isolated. In this example, a stock solution was used, which contained 7% TINUVIN® 770 (bis(2,2,6,6,-tetramethyl-4-piperidyl)sebacetate, a hindered amine stabilizer available from BASF Corp.), 30% pentanol and 63% 2-pyrrolidone. The metal bis(dithiolene) complex, $(NiS_4C_4(C_6H_5)_4)$, was added to the stock solution so that a concentration of about 2% of the metal bis(dithiolene) complex was present in the stock solution. The mixture was heated at about 100° C. until the green complex powder appeared to be reduced, as observed by a reddish brown color change, and dissolved in the stock solution. An equivalent volume of the aqueous vehicle described in Table 1 (which as described below was also used as the liquid vehicle for the fusing agent) was then added to make a formulation containing about 1% of the reduced metal bis(dithiolene) complex. Hexadecyltrimethylammonium bromide dissolved in ethanol (0.1 g/ml of ethanol) was added (in a molar equivalent to the reduced metal bis(dithiolene) complex) to the 1% formulation. Red platelets of the salt crystallized rapidly from solution. The red salt crystals were collected via vacuum filtration and recrystallized from a hot solution of acetone (5 ml) and methanol (25 ml), and had a shiny purple-red appearance. The shiny purple-red salt platelets obtained were then washed with cold methanol. The salt was tetraethylammonium nickel bis(dithiolene).

An example of a fusing agent with the shiny purple-red metal bis(dithiolene) salt was then prepared. The polar aprotic solvent used was 1-methyl-2-pyrrolidone. The shiny purple-red metal bis(dithiolene) salt were incorporated directly into a liquid vehicle (referred to as "composition 1") to form a fusing agent. The general formulation of the vehicle is shown in Table 1, with the wt % of each component that was used. The final amount of tetraethylammonium nickel dithiolene salt added to composition 1 was about 1 wt %.

TABLE 1

| Ingredient | Specific component | Vehicle (wt %) |
|---|---|---|
| Polar aprotic solvent | 1-methyl-2-pyrrolidone | 40 |
| Co-solvent | pentanol | 19 |
| Emulsifier | CRODAFOS ® O3A | 1 |
| Surface tension reduction agent | SURFYNOL ® SEF | 1.5 |

TABLE 1-continued

| Ingredient | Specific component | Vehicle (wt %) |
|---|---|---|
| Wetting agent | CAPSTONE ® FS-35 | 0.10 |
| Scale inhibitor/Anti-deceleration agent | DOWFAX ™ 2A1 | 0.20 |
| Chelating agent | TRILON ® M | 0.08 |
| Biocide | PROXEL ® GXL | 0.36 |
|  | DI (deionized) Water | Balance |

A metal bis(dithiolene) complex was prepared in a polar aprotic solvent and a thiol surfactant (referred to as "composition 2"). The metal bis(dithiolene) complex used was nickel bis(dithiolene) $(NiS_4C_4(C_6H_5)_4)$. The polar aprotic solvent used was 1-methyl-2-pyrrolidone (1M2P), and the thiol surfactant used was dodecanethiol. The general formulation of "composition 2" is shown in Table 2, with the wt % of each component that was used.

TABLE 2

| Ingredient | Specific component | Composition 1 (wt %) |
|---|---|---|
| Polar aprotic solvent | 1-methyl-2-pyrrolidone | 83 |
| Thiol surfactant | Dodecanethiol (in water) | 15 |
| Metal bis(dithiolene) complex | Nickel dithiolene | 2 |

The nickel bis(dithiolene), in the presence of dodecanethiol, was readily reduced and dissolved in the 1-methyl-2-pyrrolidone within seconds at room temperature. The nickel dithiolene changed colors from green (before reduction) to reddish brown (after reduction).

Composition 2 was incorporated into a vehicle (referred to as "composition 3") to form a first comparative fusing agent. The general formulation of the vehicle, i.e., "composition 3", is shown in Table 3, with the wt % of each component that was used.

TABLE 3

| Ingredient | Specific component | Vehicle (wt %) |
|---|---|---|
| Co-solvent | 1-methyl-2-pyrrolidone | 40 |
| Emulsifier | CRODAFOS ® O3A | 1 |
| Surface tension reduction agent | SURFYNOL ® SEF | 1.5 |
| Wetting agent | CAPSTONE ® FS-35 | 0.10 |
| Scale inhibitor/Anti-deceleration agent | DOWFAX ™ 2A1 | 0.20 |
| Chelating agent | TRILON ® M | 0.08 |
| Biocide | PROXEL ® GXL | 0.36 |
|  | DI (deionized) Water | Balance |

The first comparative fusing agent included about 50% of composition 2, about 40% of the composition 3 vehicle, and about 10% of additional deionized water (in addition to the water already present in the vehicle).

An additional composition (referred to as "composition 4") containing nickel bis(dithiolene) complex was prepared in chloroform. The general formulation of composition 4 is shown in Table 4, with the wt % of each component that was used.

TABLE 4

| Ingredient | Specific component | Composition 2 (wt %) |
|---|---|---|
| Solvent | Chloroform | 98 |
| Metal bis(dithiolene) complex | Nickel dithiolene | 2 |

Composition 4 was heated to 70° C. for 24 hours to reduce and dissolve the nickel bis(dithiolene) in the chloroform. Composition 4 was incorporated into the vehicle shown in Table 3 to form a second comparative fusing agent. The second comparative fusing agent included about 50% of composition 4, about 40% of the composition 3 vehicle, and about 10% of additional deionized water (in addition to the water already present in the vehicle).

Figure 4:
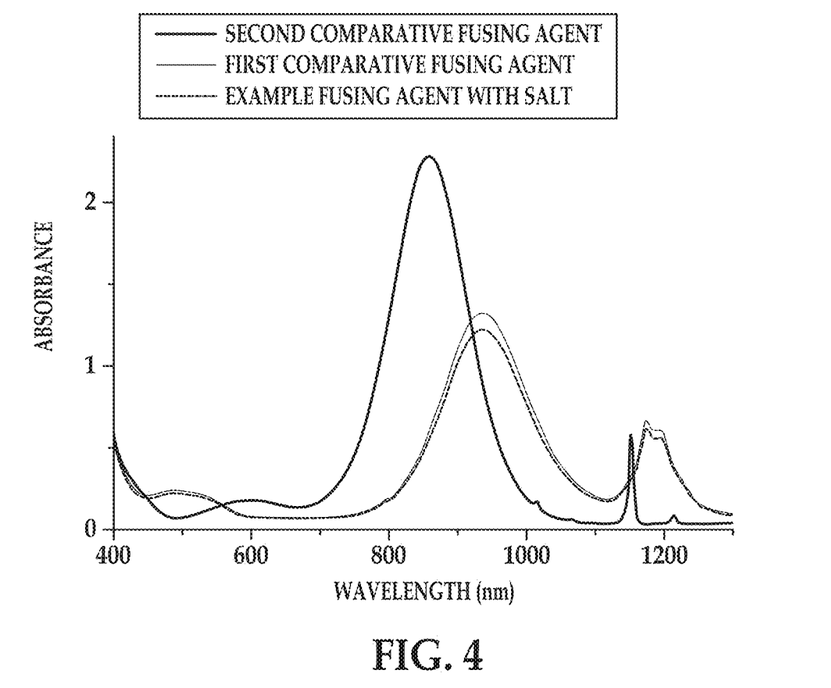
FIG. 4 is a graph depicting absorbance (y-axis) versus wavelength (nm, x-axis) of two comparative fusing agents and an example of the fusing agent disclosed herein.

The absorbance of the example fusing agent and each of the first and second comparative fusing agents was measured. The results of the absorbance measurements are shown in FIG. 4. The absorbance values are shown along the Y axis and the wavelength values in nm are shown along the X axis. As shown in FIG. 4, the maximum absorbance of the second comparative fusing agent (including the metal bis(dithiolene) complex in chloroform) was at about 850 nm. The maximum absorbance of the first comparative fusing agent (including the polar aprotic solvent, the thiol surfactant, and the metal bis(dithiolene) complex) shifted to about 940 nm. The maximum absorbance of the example fusing agent (including the nickel bis(dithiolene) salt in the liquid vehicle including the polar aprotic solvent) was also about 940 nm (similar to the first comparative fusing agent), which represents about a 90 nm shift in the absorbance maximum from that of the metal bis(dithiolene) complex in chloroform (i.e., the second comparative fusing agent).

The profiles in FIG. 4 illustrate that when dissolved in a polar aprotic solvent, the absorption characteristics of dithiolene moieties in metal bis(dithiolene) salt is comparable to the absorption characteristics of dithiolene moieties in metal bis(dithiolene) complex.

Example 2

Example 3D parts, namely dog bones, were printed. The build material used to print the example parts was polyamide-12 (PA-12). The fusing agent used to print the example parts was the example fusing agent from Example 1 (which contained nickel bis(dithiolene) salt, 1-methyl-2-pyrrolidone, as well as other vehicle components and additional DI water). The fusing agent exhibited a reddish brown color, in part because the water prevented (further) reduction of the metal bis(dithiolene) anion component.

For each example part, the example fusing agent was thermal inkjet printed with a HP761 printhead (manufactured by Hewlett-Packard Company) in a pattern on a portion of the PA-12 in subsequent layers. Each layer was about 100 µm in thickness. New layers were spread onto the fabrication bed from a supply region using a roller. The temperature of the supply region was set at 115° C. The temperature of the printing region was set at 155° C. with a platen underneath it heated to 148° C. The example parts were printed at a contone level ranging from about 20 contone to about 128 contone (which refers to the number of drops, which is divided by 256, that will be placed on average onto each pixel). The example parts were then exposed to high-intensity light from a halogen lamp with a power ranging from about 500 watts to 750 watts and a color temperature ranging from about 2700 K to about 3400 K passing over the fabrication bed with a fusing speed ranging from about 20 inches per second (ips) to about 30 ips. After all layers were printed, the example parts were removed from the fabrication bed and sandblasted to remove excess powder. The example parts were not subjected to any further post treatment.

Figure 5:
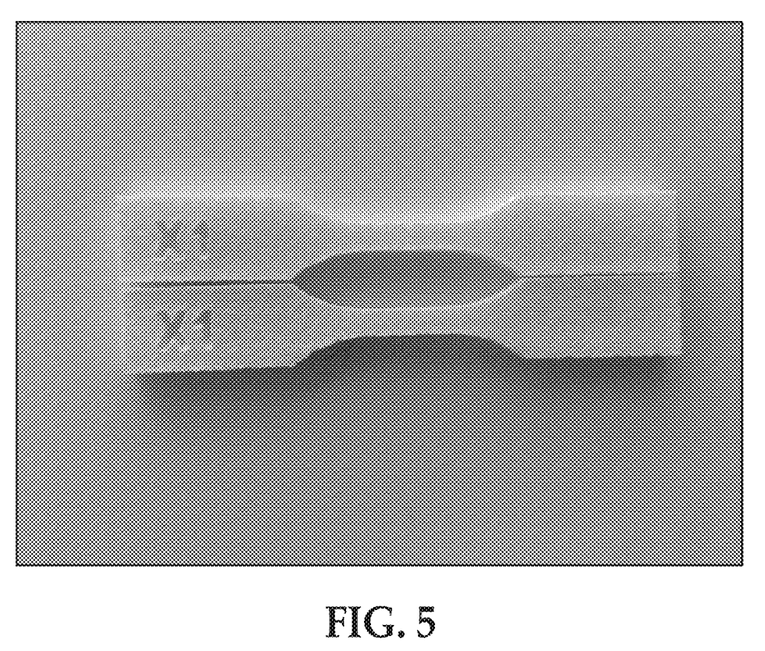
FIG. 5 is a black and white representation of an originally colored photographic image of example 3D printed parts, formed with examples of the fusing agent and 3D printing method disclosed herein.

FIG. 5 shows two of the printed dog bones in black and white. The tensile strength of the dog bones was not tested. However, based on the density and the black point temperature during printing, the tensile strength should have been about 40 MPa. The example parts as formed had vivid white color. During and/or after fusing (as water is driven off), the metal bis(dithiolene) anion component was further reduced from its reddish brown form to its colorless form. The originally colored photographs show the bright white color.

It is to be understood that the ranges provided herein include the stated range and any value or sub-range within the stated range. For example, a range from about 1 wt % to about 3 wt % should be interpreted to include not only the explicitly recited limits of from about 1 wt % to about 3 wt %, but also to include individual values, such as 1.35 wt %, 1.55 wt %, 2.5 wt %, 2.85 wt %, etc., and sub-ranges, such as from about 1.35 wt % to about 2.5 wt %, from about 1.5 wt % to about 2.7 wt %, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A fusing agent, comprising:
   a liquid vehicle including:
   a polar aprotic solvent;
   a thiol surfactant selected from the group consisting of dodecanethiol, 1-undecanethiol, 2-ethylhexanethiol, 1-octanethiol, 1-tetradecanethiol, and combinations thereof; and
   a balance of water; and
   a metal bis(dithiolene) salt dissolved or dispersed in the liquid vehicle.

2. The fusing agent as defined in claim 1 wherein the metal bis(dithiolene) salt has a general formula I:

wherein:
M is a metal selected from the group consisting of nickel, zinc, platinum, palladium, and molybdenum;

each of W, X, Y, and Z is selected from the group consisting of H, Ph, PhR, and SR, wherein Ph is a phenyl group and R is selected from the group consisting of $C_nH_{2n+1}$, $OC_nH_{2n+1}$, and $N(CH_3)_2$, wherein $2 \leq n \leq 12$; and the [Cat]$^+$ is a cation of a nitrogen base.

3. The fusing agent as defined in claim 1 wherein the polar aprotic solvent is selected from the group consisting of 1-methyl-2-pyrrolidone, 2-pyrrolidone, 1-(2-hydroxyethyl)-2-pyrrolidone, dimethylformamide (DMF), dimethyl sulfoxide (DMSO), and a combination thereof.

4. The fusing agent as defined in claim 1, further comprising a colorant.

5. The fusing agent as defined in claim 1, further comprising an additive selected from the group consisting of a water soluble organic solvent, an emulsifier, a surface tension reduction agent, a wetting agent, a scale inhibitor, an anti-deceleration agent, a chelating agent, an antimicrobial agent, and a combination thereof.

6. The fusing agent as defined in claim 1 wherein:
the metal bis(dithiolene) salt is present in an amount ranging from about 1 wt % to about 3 wt % based on a total weight of the fusing agent; and
the polar aprotic solvent is present in an amount ranging from about 5 wt % to about 50 wt % based on the total weight of the fusing agent.

7. A method for making a fusing agent, comprising:
exposing a metal bis(dithiolene) complex to a solution including a reducing agent, thereby forming a reduced metal bis(dithiolene) complex dissolved in the solution;
diluting the solution with an aqueous vehicle so that the reduced metal bis(dithiolene) complex is present in the diluted solution in an amount ranging from about 1% to about 3% by weight;
adding a nitrogen base to the diluted solution, thereby reacting the reduced metal bis(dithiolene) complex with the nitrogen base and forming metal bis(dithiolene) salt crystals;
collecting the metal bis(dithiolene) salt crystals; and
adding the metal bis(dithiolene) salt crystals into a liquid vehicle including at least a polar aprotic solvent and water.

8. The method as defined in claim 7 wherein the nitrogen base is selected from the group consisting of tetraethyl ammonium bromide, hydrazine, piperidine, pyridine, hexadecyltrimethylammonium bromide, and combinations thereof.

9. The method as defined in claim 7 wherein the metal bis(dithiolene) salt crystals have a general formula I:

wherein:
M is a metal selected from the group consisting of nickel, zinc, platinum, palladium, and molybdenum;
each of W, X, Y, and Z is selected from the group consisting of H, Ph, PhR, and SR, wherein Ph is a phenyl group and R is selected from the group consisting of $C_nH_{2n+1}$, $OC_nH_{2n+1}$, and $N(CH_3)_2$, wherein $2 \leq n \leq 12$; and the [Cat] is a cation of a nitrogen base.

10. The method as defined in claim 7 wherein the addition of the metal bis(dithiolene) salt crystals into the liquid vehicle is accomplished at a temperature ranging from about 18° C. to about 25° C.

11. The method as defined in claim 7 wherein the polar aprotic solvent is selected from the group consisting of 1-methyl-2-pyrrolidone, 2-pyrrolidone, 1-(2-hydroxyethyl)-2-pyrrolidone, dimethylformamide (DMF), dimethyl sulfoxide (DMSO), and a combination thereof.

* * * * *